United States Patent
Woodward et al.

(10) Patent No.: US 6,713,268 B2
(45) Date of Patent: Mar. 30, 2004

(54) METHODS OF IDENTIFYING OCULAR HYPOTENSIVE COMPOUNDS HAVING REDUCED HYPERPIGMENTATION

(75) Inventors: David F. Woodward, Lake Forest, CA (US); Licheng Shi, Irvine, CA (US); Achim H-P Krauss, Foothill Ranch, CA (US); Clayton S. Spada, Fullerton, CA (US); Sheila Mac Neil, Sheffield (GB); Linda C. Smith-Thomas, Sheffield (GB)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 09/893,159

(22) Filed: Jun. 26, 2001

(65) Prior Publication Data

US 2003/0018078 A1 Jan. 23, 2003

(51) Int. Cl.$^7$ ..................... G01N 33/53; G01N 33/567; C12N 5/06; C12P 31/00; C07C 59/147
(52) U.S. Cl. ................. 435/7.2; 435/357; 435/63; 554/117; 549/422
(58) Field of Search ............... 435/7.2, 357, 63; 554/117; 549/422

(56) References Cited

U.S. PATENT DOCUMENTS 5,688,819 A    11/1997   Woodward et al.
6,458,836 B1 * 10/2002   Ueno

FOREIGN PATENT DOCUMENTS

WO       WO 94/06433       3/1994

OTHER PUBLICATIONS

Ozeki H, et al. Biochim. Biophys. Acta. 1336:539–548, 1997.*
Boni R, et al. Br. J. Dermatol. 137:96–100, 1997.*
Watson et al, Ophthalmology, "A Six–month, Randomized, Double–masked Study Comparing Latanoprost with Timolol in Open–angle Glaucoma and Ocular Hypertension", 103:126–132 (1996).
Hearing B.J., et al, Faseb J., "Enzymatic control of pigmentation in mammals", (1991) 5: 2902–2909.
Morelli, J.G., et al, J. Invest Dermatol., "Influence of Inflammatory Mediators and Cytokines on Human Melanocyte Function", (1993) 100:191S–195S.
Aroca, P., et al, J. Biol. Chem., "Melanin Biosynthesis Patterns following Hormonal Stimulation", (1993) 268: No. 268, 25650–25655.
Krauss, A.H.–P., et al, ARVO abstracts 39: S804 (1998).
Shi, L., et al, PASPCR abstracts 11: 186 (1998).
Krauss, A.H.–P, et al., Internat. Congress of Eye Res. Abstracts 14:S78 (2000).
Krauss, A.H.–P., et al, ARVO abstracts 41: S250 (2000).
Krauss, A.H.–P., et al, IPCC abstracts Supp. 7, 68 (1999).

* cited by examiner

*Primary Examiner*—Gary Kunz
(74) *Attorney, Agent, or Firm*—Carlos A. Fisher; Martin A. Voet; Robert J. Baran

(57) ABSTRACT

Methods to identify agents having ocular hypotensive activity which have reduced or absent ability to stimulate iridial hyperpigmentation are disclosed. The methods reside in part in detecting the ability of a test compound to interact with the FP receptor.

6 Claims, 4 Drawing Sheets

METHODS OF IDENTIFYING OCULAR HYPOTENSIVE COMPOUNDS HAVING REDUCED HYPERPIGMENTATION

TECHNICAL FIELD

The invention relates primarily to the treatment of ocular hypertension, such as that associated with glaucoma, with agents comprising prostaglandin analogs or derivatives wherein treatment with the agent results in minimal or absent ocular hyperpigmentation effects. Additionally, the invention concerns methods to identify and design prostaglandin F analogs which lack the ability to effect hyperpigmentation.

BACKGROUND OF THE INVENTION

Certain prostaglandins and their analogs and derivatives, such as the $PGF_{2\alpha}$ derivative latanoprost, sold under the trademark XALATAN®, have been established as compounds useful in treating ocular hypertension and glaucoma. However, latanoprost, the first prostaglandin approved by the United States Food And Drug Administration for this indication, is a prostaglandin derivative possessing the undesirable side effect of producing an increase in brown pigment in the iris of 5–15% of human eyes. The change in color results from an increased number of melanosomes (pigment granules) within iridial melanocytes. See e.g., Watson et al., *Ophthalmology* 103:126 (1996) (this and all references cited herein are incorporated by reference). While it is still unclear whether this effect has additional and deleterious clinical ramifications, from a cosmetic standpoint alone such side effects are undesirable.

It would be desirable to devise methods of treating a patient having glaucoma with a prostaglandin, prostaglandin analog or prostaglandin derivative that either lacks or has a reduced ability to stimulate an increase in iridial pigmentation as compared to a synthetic ocular hypertensive prostaglandin derivative, such as latanoprost. By prostaglandin derivative is meant a compound having structural similarity to a prostaglandin, preferably a PGF prostaglandin, having carboxylic acid groups, and esters thereof.

It would additionally be desirable to have a method for identifying compounds that are useful for the treatment of ocular hypertension which do not have this undesirable side effect. The present invention provides a method to design and identify $PGF_{2\alpha}$ analogs and/or derivatives which are useful in lowering ocular pressure, but which substantially lack this undesired side effect, as well as methods of glaucoma treatment with such compounds.

It is known that pigmentation in the iris is due to formation of melanin and that the most essential enzyme in melanin biosynthetic pathway is tyrosinase; tyrosine is absolutely required for melanin production. See, for example, Hearing B. J., et al., *FASEB J.* (1991) 5:2902–2909. Melanin is typically synthesized in melanocytes and the effects of various factors on melanin production in melanocytes has been studied, for example, by Morelli, J. G., et al., *J. Invest Dermatol* (1993) 100:191S–195S. In addition, it has been shown that although melanocyte-stimulating hormone (MSH) appears to stimulate the activity of tyrosinase in melanocytes, MSH does not increase the expression or activity of other enzymes involved in the melanin biosynthetic pathway, specifically the enzymes designated TRP2 and TRP1. Aroca, P., et al., *J. Biol. Chem.* (1993) 268:25650–25655.

Attempts have been made to evaluate the mechanism for pigmentation stimulation by studying the effects of prostaglandins and analogs or derivatives thereof on melanogenesis and cell proliferation in the S91 "Cloudman" melanoma cell line. Using this cell line, Krauss and co-workers (Krauss, A. H.-P., et al., *ARVO* abstracts 39:S804 (1998)) demonstrated that although MSH was able to simulate melanogenesis in a predictable way, $PGF_{2\alpha}$ and similar compounds were able to stimulate melanin production in this melanoma cell line only at quite high concentrations, indicating the involvement of receptors other than the natural PGF2α receptor, FP. Treatment of cells with butaprost and ligands for prostaglandin receptors other than FP indicated the involvement of $EP_2$ and IP receptors. These studies indicated that S91 cells contain $EP_2$ and IP receptors, but not FP receptors, which are known to respond to latanoprost. This was further reported by Shi, L., et al., *PASPCR* abstracts 11:186(1998).

Subsequent studies by Krauss, A. H.-P, et al., *Internat. Congress of Eye Res.* Abstracts 14:S78(2000) showed that FP receptors were absent in S91 cells, as RT-PCR failed to amplify FP receptor mRNA and stimulation with PGF2α (the natural ligand for the FP receptor) failed to stimulate a calcium signal. When these cells were stably transfected with an FP receptor and permitted to overexpress the protein, RT-PCR produced FP receptor cDNA and the receptor was displayed on the cell surface. However, $PGF_{2\alpha}$, did not generate a calcium signal in these transfected S91 cells. A calcium signal is typically associated with FP receptor stimulation in other cells. The effects of $PGF_{2\alpha}$ on DOPA oxidase (tyrosinase) activity and melanin formation in these FP receptor transfectants were indistinguishable from the responses contained in native, untransfected S91 cells. Krauss, A. H.-P., et al., *ARVO* abstracts 41:S250 (2000); Krauss, A. H.-P., et al., *IPCC* abstracts Supp. 7, 68(1999). Thus, these data suggest that although melanocytes lack significant FP receptor expression (which $PGF_{2\alpha}$ is known to stimulate), modifying these cells to provide this receptor is not sufficient to remedy the inability of melanocytes to synthesize melanin in response to this prostaglandin or its analogs.

It has now been found that in order for $PGF_{2\alpha}$ to stimulate melanin production in cell culture, the medium in which the melanocytes are thus affected must contain fibroblasts. Based on this knowledge, it is possible to identify and design compounds which will reduce intraocular pressure, while lacking the side effect of hyperpigmentation.

SUMMARY OF THE INVENTION

The invention takes advantage of the discovery that the mechanism for melanin production resulting from treatment with prostaglandin analogs involves an intermediate step, specifically thought to be agonism by the analog on the FP receptor of fibroblasts, or cells of fibroblast lineage in the presence of melanocytes (or melanocyte-derived cells), probably followed by the fibroblasts' elaboration of a soluble signal detectable by the melanocytes which in turn serves to stimulate melanin production.

In one embodiment of the invention, compounds are assayed for their ability to stimulate the FP receptor population present on fibroblasts. Detection of FP receptor activity may be direct or indirect. Compounds which fail to stimulate the FP receptor expressed in fibroblasts but which are nevertheless able to control intraocular pressure are suitable candidates for the design of therapeutic agents exhibiting absent or reduced hyperpigmentation.

In another embodiment of the invention, the present inventors have discovered that prostaglandin analogs that are non-acidic—i.e., lack the carboxyl group characteristic of PGF$_{2\alpha}$, are unable to stimulate the FP receptor. Thus, compounds can be designed for glaucoma treatment which are neutral or basic at physiological pH and such compounds will exhibit reduced or absent hyperpigmentation.

Thus, in one aspect, the invention is directed to a method of identifying a compound comprising a prostaglandin, prostaglandin derivative or prostaglandin analog capable of lowering intraocular pressure which compound lacks the undesirable property of stimulating iridial hyperpigmentation, said method comprising contacting said compound with fibroblast cells expressing the FP receptor and directly or indirectly assessing the ability of the compound to stimulate said FP receptor, wherein a failure to stimulate the FP receptor is an indication that said compound lacks said property.

As indicated, the determination of whether FP receptor activity is stimulated may be direct, as for example, by detecting stimulation of an intracellular Ca$^{++}$ signal, or may be indirect. Such indirect means may include detecting the presence or absence of a compound or physical phenomenon whose presence or absence, respectively, is characteristic of FP receptor stimulation.

In a preferred embodiment of the invention fibroblasts and melanocytes (or melanoma cells) are co-cultured in the presence of a test compound, and the synthesis of melanin by the melanocyte is compared with the synthesis of melanin in a control culture, e.g., by the same cell type in a similar cell co-culture in the absence of the test compound, or by the same cell type and agent incubated in the absence of fibroblasts. Melanin production can be detected directly or indirectly. Direct detection methods include, without limitation, extraction and detection of melanin (including either or both eu-malanin or phaeo-melanin) from the incubated melanocytes, HPLC analysis of a melanocyte lysate, correlation of a peak (or absence thereof) with a melanin standard, observation of light absorbency in a cell lysate at a wavelength characteristic of melanin, and radiolabeling of melanin precursors and detection of radiolabeled melanin following stimulation. Indirect detection includes, without limitation, detection of tyrosinase activity in the melanocytes. Currently this latter method is preferred by the Applicants.

The fibroblasts and melanocytes used in the assays of the present invention may be primary cells or may be immortal cell lines derived from these primary cell types. Preferably the cells are immortal cell lines derived from each of the two cell types.

In another embodiment, the invention is directed to a method to select intraocular pressure-lowering PGF$_{2\alpha}$ analogs or derivatives which display absent or reduced iridial pigmentation when compared to a standard, preferably latanoprost free acid, comprising designing a prostaglandin F$_{2\alpha}$ analog or derivative which is neutral or basic rather than acidic. A large number of prostaglandin analogs and derivatives are known. Many are set forth, for example, in International Patent Publication No. WO 94/06433 and U.S. Pat. No. 5,688,819, both incorporated herein by reference in their entirety. Many such compounds are commercially available, including latanoprost, fluprostenol (both of which contain carboxylic acid functions and thus according to the present invention would be expected to stimulate iridial hyperpigmentation). Other analogs are available for synthesis, such as prostamide F$_{2\alpha}$ and other non-acidic analogs such as, without limitation, those set forth below. Finally, arachidonic acid and anandamide are biosynthetic precursors of various prostaglandins and prostamides, respectively.

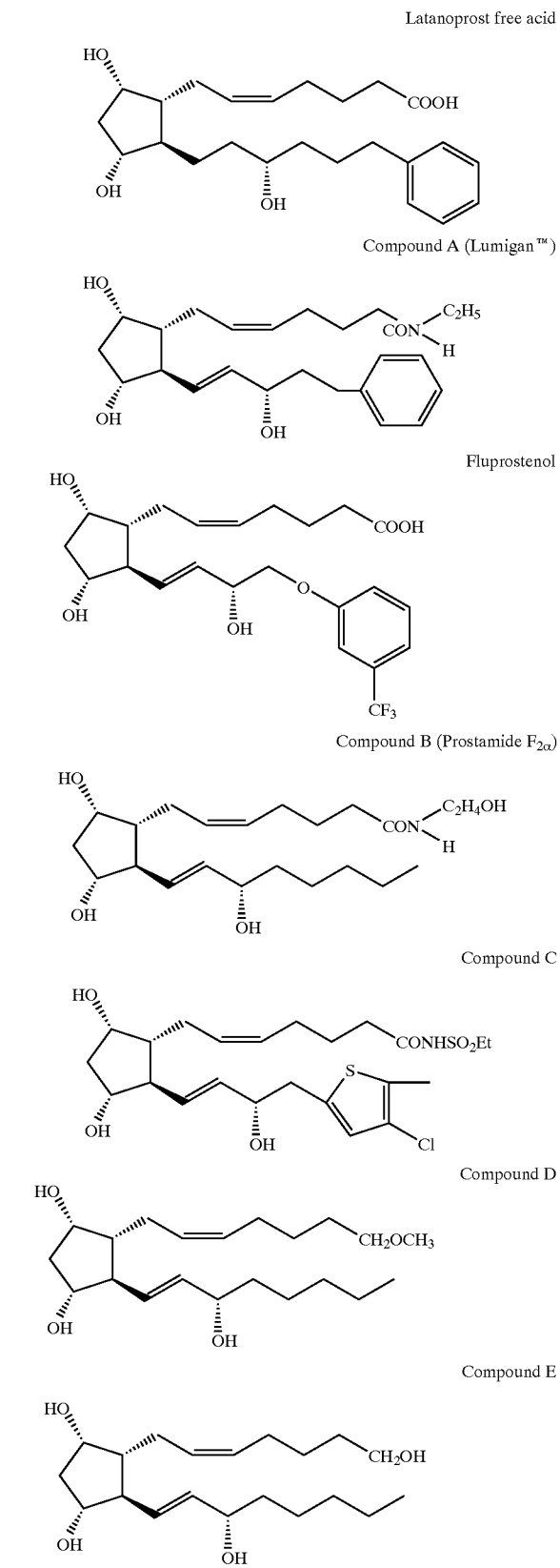

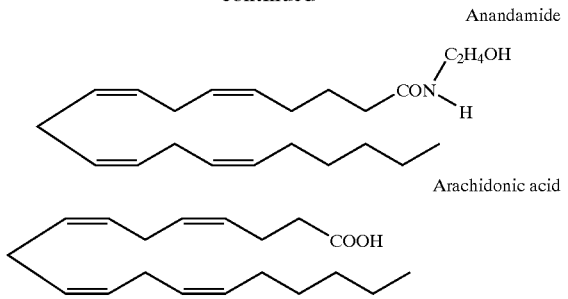

Anandamide

Arachidonic acid

By taking advantage of the invention disclosed herein, it is possible to predict which of these analogs, and any newly synthesized analogs or derivatives, will have lessened or absent ability to stimulate hyperpigmentation.

DETAILED DESCRIPTION OF THE INVENTION

Figure 1:
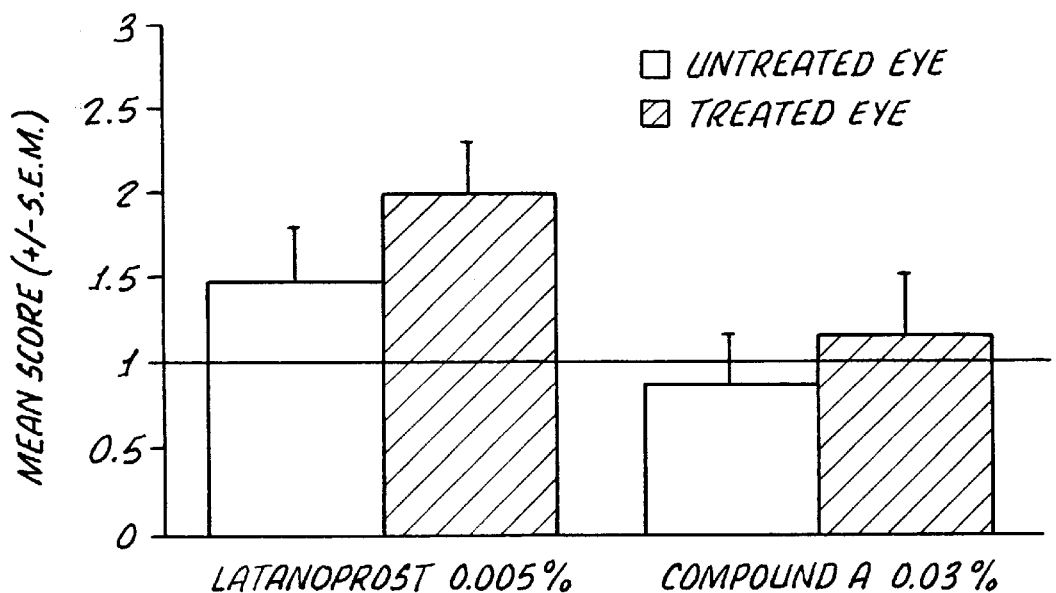
FIG. 1 is a graphical depiction of the results on a one year study in which monkeys were given topical administration of either latanoprost or Compound A (Lumigan™) in one eye daily over a one year time period. The results are rated as to darkening of the iris with 0 indicating no change and 3 indicating severe iridial darkening.

The ocular hypotensive compounds useful in the invention as having absent or reduced ability to stimulate iridial hyperpigmentation can be identified by assessing their ability to stimulate the FP receptor preferably as displayed on fibroblasts. In this first aspect, the compound will be separately tested, preferably before applying the methods of the present invention, and confirmed to be an agent capable of lowering intraocular pressure (IOP). Such agents may also be useful in the treatment of ocular hypertensive conditions other than glaucoma, such as post-surgical and post-laser trabeculectomy ocular hypertensive episodes, and as presurgical adjuncts. Also, the agents may be useful in the treatment of various pathophysiological diseases including acute myocardial infarction, vascular thrombosis, hypertension, pulmonary hypertension, ischemic heart disease, congestive heat failure, and angina pectoris, in which case the compounds may be administered by any means that effect vasodilation and thereby relieve the symptoms of the disease. For example, administration may be by oral, transdermal, parenterial, subcutaneous, intravenous, intramuscular, intraperitoneal, transdermal, or buccal routes.

Those anti-glaucoma agents which are able to stimulate the FP receptor, preferably on fibroblasts, will stimulate iridial hyperpigmentation; those which fail to stimulate the receptor are identified as giving rise to lessened, or absent hyperpigmentation. Assessment of this ability can be carried out in a number of ways. For example, melanin production can be detected within melanocytes co-cultured with fibroblasts in the presence of the test compound (for example, by measuring the absorbance of lysates of treated versus untreated cells at a wavelength characteristic for melanin), or tyrosinase activity within these cells can be measured. Such cells may be co-cultured in transwells. When melanocytes or melanoma cells are co-cultured with fibroblasts, the former should be in excess over the latter.

Alternatively, stimulation of the FP receptor borne by the cultured fibroblasts can be detected, as, for example, by detecting an intracellular $Ca^{++}$ signal. Compounds which are found to stimulate the receptor less than a standard hyperpigmentation-stimulating prostaglandin derivative, for example latanoprost free acid or fluprostanol, are thus selected for synthesis and formulation into pharmaceutical compositions for treatment of ocular hypertension.

It has also now been found that compounds which are $PGF_{2\alpha}$ analogs but which are not acidic do not stimulate melanin synthesis, or have a reduced ability to do so and may be formulated for the treatment of ocular hypertension. Thus, in another alternative, pharmaceutical compositions can be prepared having as active ingredients compounds which are prostaglandin analogs lacking this acidic property.

The pharmaceutical compositions identified by the methods of the invention can be formulated using standard techniques for administration to subjects for the treatment of glaucoma. Such formulations are found in Remington's *Pharmaceutical Sciences*, latest edition, Mack Publishing Co., Easton, Pa., incorporated herein by reference. Suitable formulations include both systemic formulations and localized application, most typically eye drops. The dosage levels and modes of administration are readily optimized using standard techniques understood by practitioners of the art. The dosage levels will vary depending on the nature of the condition in the subject, the judgment of the practitioner, and the formulation and mode of administration.

The following example is intended to illustrate but not to limit the invention.

EXAMPLE 1

Materials and Methods

Human dermal fibroblasts and S91 melanoma cells are cultured in low-glucose Dulbecco's Modified Eagle Medium (DMEM) containing 10% fetal calf serum (FCS) supplemented with 2 mM L-glutamine, 100 mg/l sodium pyruvate, 100 U/ml penicillin G, 100 U/ml streptomycin and 250 ng/ml amphotericin B at 37° C. with 5% $CO_2$. For tyrosinase and melanogenesis assays, the FCS concentration is reduced to 1% during the incubation period.

S91 cells are plated at $10^5$ cells/well in 6-well plates and allowed to attach overnight. For transwell studies, cells from a human dermal fibroblast cell line are plated on the transwell insert at $10^3$ cells/well and allowed to attach overnight. Melanoma cells are plated in an initial excess over fibroblasts; preferably at a ratio between about 1:30 and about 1:1000, more preferably at a ratio between about 1:50 and about 1:300; most preferably at a ratio of about 1:100. For primary cells, cells are cultured at a ratio of fibroblasts to melanocytes of about 1:2 to about 1:50; preferably about 1:5 to about 1:20, even more preferably about 1:10. The added test agents generally stimulate fibroblast proliferation; thus the use of the transwell permits separate enumeration of the melanocytes.

Test agents are added every other day of the assay period, with no exchange of medium.

For the melanin assay, cells were incubated for 5 days. At the end of the incubation period, S91 cells were harvested and dissolved in 1 M NaOH by overnight incubation at 37° C. in a shaking water bath. After centrifugation for 30 min at 16,000×g at room temperature, the optical density of the supernatant was measured at 475 nm and compared to a standard curve obtained with synthetic melanin.

For DOPA oxidase (tyrosinase) activity, the cells were incubated for four days in this case and the S91 cells were collected in a lysis buffer. The cell suspension was subjected to one freeze/thaw cycle (−80° C.) and vortexed to extract the cytosolic cell contents. After centrifugation for 30 minutes at 16,000×g at 4° C., aliquots of the supernatant were used in a Bradford assay to determine protein concentration or incubated with d-DOPA or l-DOPA as substrates. The optical density was measured for up to 6 hours at 490 nm.

For the cell proliferation assay, melanoma cells were washed with Hanks BSS, trypsinized and counted with a hemacytometer.

EXAMPLE 2

In one experiment, monkeys are treated once daily with a 35 microliter drop in one eye with either 0.005% (w/v) latanoprost or 0.03% Compound A for one year. The other eye is left untreated. A total of 8 animals is treated within each treatment group. At the end of the one year study period darkening of the treated eye is compared to a photograph of the same eye prior to treatment, and scored using the following scale:

0 no change
1 subtle, barely perceptable change
2 moderate, easily noticeable change
3 severe, significant change The results are shown in FIG. 1. As can be seen, the untreated eyes showed some age-related darkening in the absence of either agent, and the baseline for the experiments was therefore 1. The latanoprost-treated eyes were noticeably darker, with a score of 2. By contrast, eyes treated with Compound A, were significantly less dark (average score= about 1.1).

Thus, these results confirm that melanin production and iridial hyperpigmentation is significantly lessened when an eye is treated with Compound A as compared to latanoprost.

EXAMPLE 3

Human embryonic kidney cells of line HEK-293 are stably transfected with an expression vector encoding the human FP receptor. Cells were cultured in low Glucose Dulbecco's Modified Eagles Medium containing 10% fetal calf serum, 2 mM L-glutamine, 100 mg/l sodium pyruvate, 100 U/ml penicillin G, 100 U/ml streptomycin, 250 µg/ml G418 200 µg/ml hygromycin and 250 ng/ml amphotericin B at 37° C. with 5% $CO_2$. Cells were seeded on poly-D-lysine-coated 96-well plates at 5000/well, and cultured overnight before the experiment. The cells are cultured in the presence, respectively, of: latanoprost-free acid, fluprostenol, Compound A, Compound B, and assayed using a FLIPR (fluorescence imaging plate reader) using the calcium activated fluorescent dye Fluo-4 as an indicator of free intracellular calcium. As stimulation of the FP receptor is known to cause in increase in free intracellular calcium release, this experiment is designed to determine when the test compounds are capable of stimulating the human FP receptor.

Figure 2:
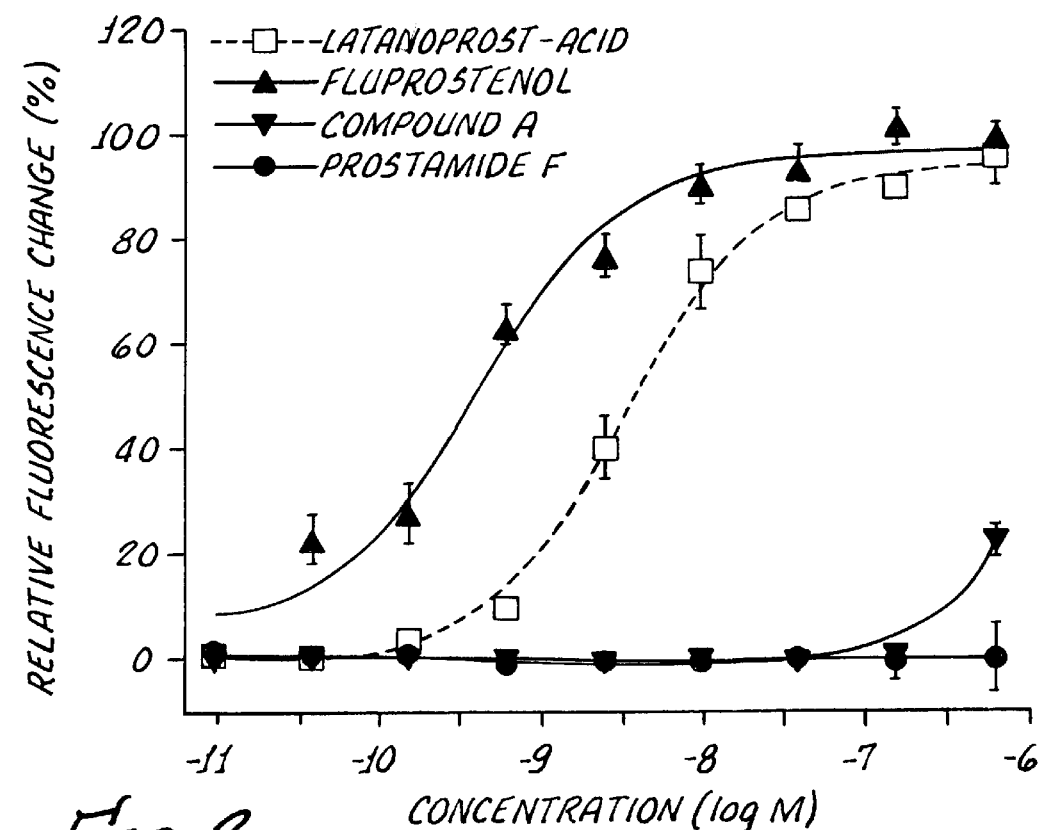
FIG. 2 is a plot showing calcium signaling within human embryonic kidney cells transfected with an expression plasmid encoding the human prostaglandin FP receptor in response to treatment with latanoprost, fluprostenol, Compound A or Compound B (prostamide F2α). The data indicate that the former two agents stimulate the FP receptor, while the latter two agents do not stimulate the FP receptor.

FIG. 2 shows that latanoprost and fluprostenol are capable of stimulating the FP receptor at concentrations of about $10^{-11}$M and that this effect plateaus at about $10^{-8}$M. By contrast, both prostamide F2α and Compound A do not stimulate the human FP receptor at these concentrations.

EXAMPLE 4

Cloudman S91 melanoma cells (ATCC CCL-53.1) were cultured either in the presence or absence of human dermal fibroblast cells (ATCC CRL-2097) as described above. The added drugs were: arachidonic acid, anandamide, Compound C, Compound A, Compound D, Compound C, and Compound E.

Figure 3A:
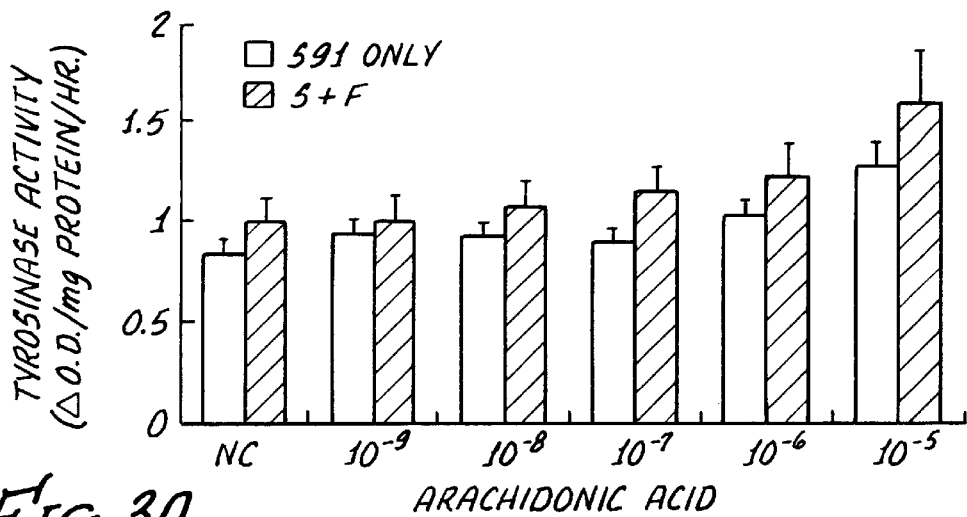
FIGS. 3A–3F are bar graphs showing the effect upon melanoma cells upon culture in the presence of increasing concentrations of arachidonic acid, anandamide, Compound C, Compound A, Compound D, and Compound E, respectively. The graphs show results for S91 melanoma cells cultured alone or in transwell culture with a human dermal fibroblast cell line.

As indicated in FIG. 3A, cells cultured in the presence of from $10^{-9}$ to $10^{-5}$ M arachidonic acid (a prostaglandin precursor) show a significant increase in tyrosinase (DOPA oxidase) activity as a function of increasing dose; a smaller increase is seen in cultures of melanoma cells without added fibroblasts, although at most doses this increase is not statistically significant.

Figure 3B:
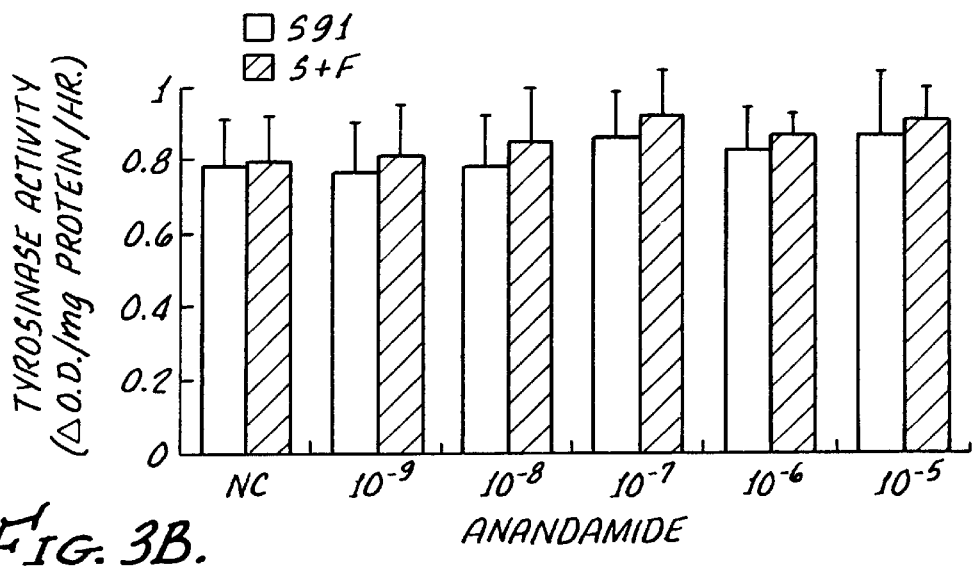

By contrast, FIG. 3B shows the results of an identical experiment in which cells are exposed to anandamide (a prostamide precursor) rather than arachidonic acid. This experiment demonstrates that there is no significant increase in tyrosinase activity as a result of exposure to increasing amounts of the drug.

Figure 3C:
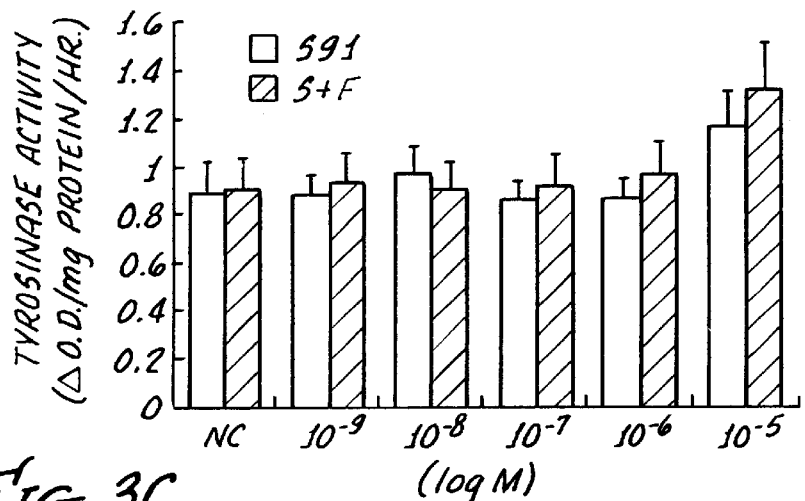

FIG. 3C shows the results of a similar experiment in which the cultures are grown in the presence of Compound C, another prostamide. Tyrosinase activity does not change significantly between dosage levels of $10^{-9}$ to $10^{-5}$ M. A small increase in tyrosinase activity at $10^{-5}$M is probably due to non-specific interactions of the drug with the target cells due to the presence of the drug at relatively high concentrations.

Figure 3D:
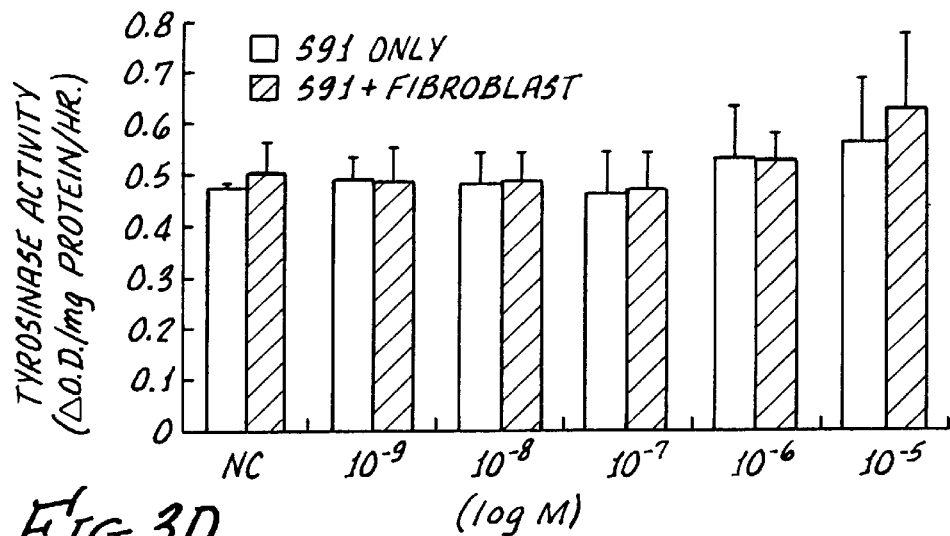

Similarly, FIG. 3D shows tyrosinase activity data for cultures in the presence of COMPOUND A, a prostamide. In this experiment there are no significant changes in tyrosinase activity at any drug concentration tested.

Figure 3E:
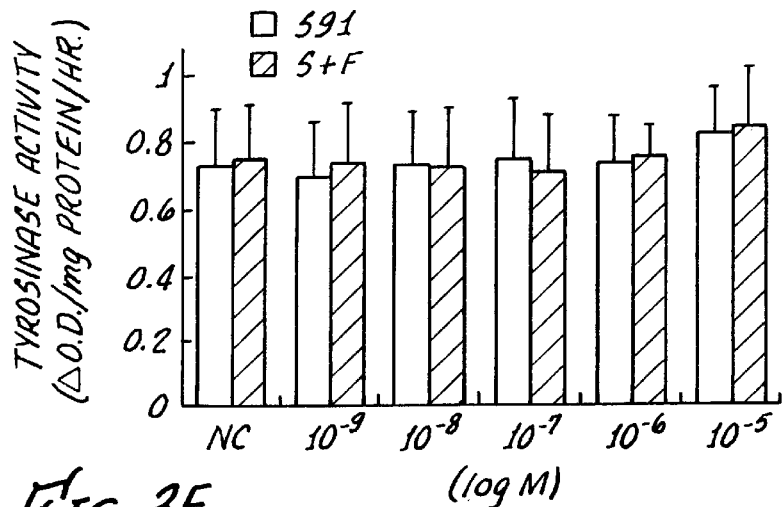

FIG. 3E shows similar data for Compound D. The drug, which lacks a carboxylic acid group, causes no significant stimulation of tyrosinase activity in this assay.

Figure 3F:
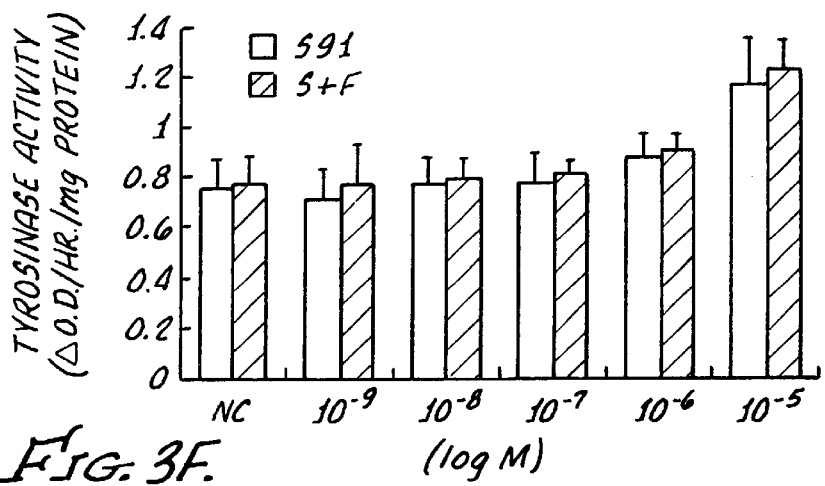

FIG. 3F shows similar data for Compound E. In this case there is a small decrease in cell number at the higher concentrations (data not shown), but only the highest dose ($10^{-5}$ M) shows an increase in tyrosinase activity, again, probably due to the non-specific activation of receptors at such high concentrations of test compound.

In the experiment in which a significant increase in tyrosinase activity was seen (i.e., FIG. 3A), the co-culture of fibroblasts and melanoma cells gave rise to significantly greater tyrosinase activity increases than was seen in the presence of melanoma cells alone.

Assessment of cell proliferation was used as a control; the presence of fibroblasts did not affect the impact of these compounds (if any) on cell proliferation.

EXAMPLE 5

In an experiment conducted identically to that of Example 4, the compounds tested were latanoprost-free acid, fluprostenol, and prostamide $F_{2\alpha}$ (Compound B). In a range of concentrations of $10^{-9}$ to $10^{-6}$ M, latanoprost had little effect on S91 cell proliferation whether fibroblasts were included in the transwell co-culture or not. At a concentration of $10^{-5}$ M, a decrease was observed in both cases. No effect on cell proliferation by either fluprostenol or prostamide $F_{2\alpha}$ was seen in the range of $10^{-9}$ to $10^{-5}$ M with or without fibroblast co-cultures.

Figure 4A:
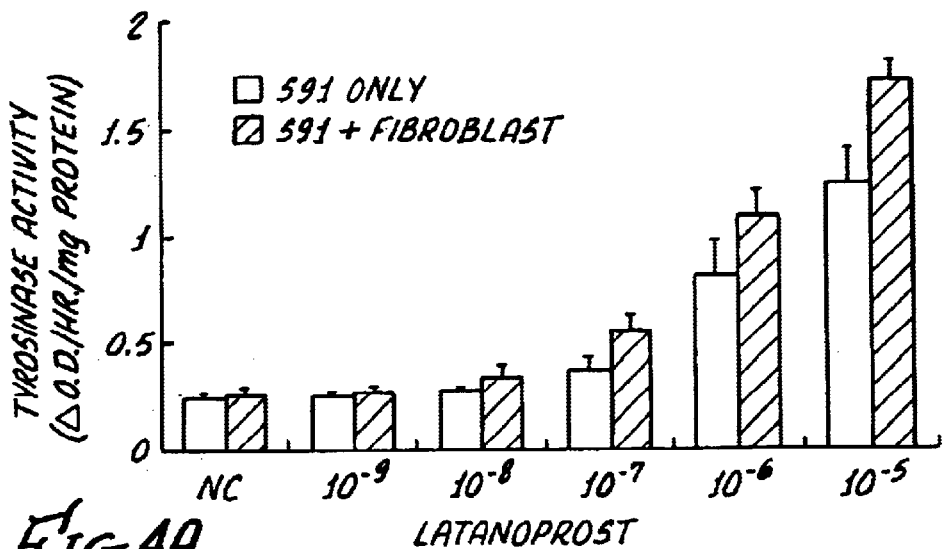
FIGS. 4A, 4B and 4C are graphic representations of the effects of latanoprost, fluprostenol, and prostamide F2α (Compound B), respectively, on tyrosinase activity in S91 fibroblast transwell co-cultures with melanoma cells. As shown, latanoprost and fluprostenol stimulate increased production of tyrosinase in these cells when they are cultured in the presence of fibroblasts. No significant dose-dependent stimulation of tyrosinase activity is shown by prostamide F2α in the absence or presence of co-cultured fibroblasts.
Figure 4B:
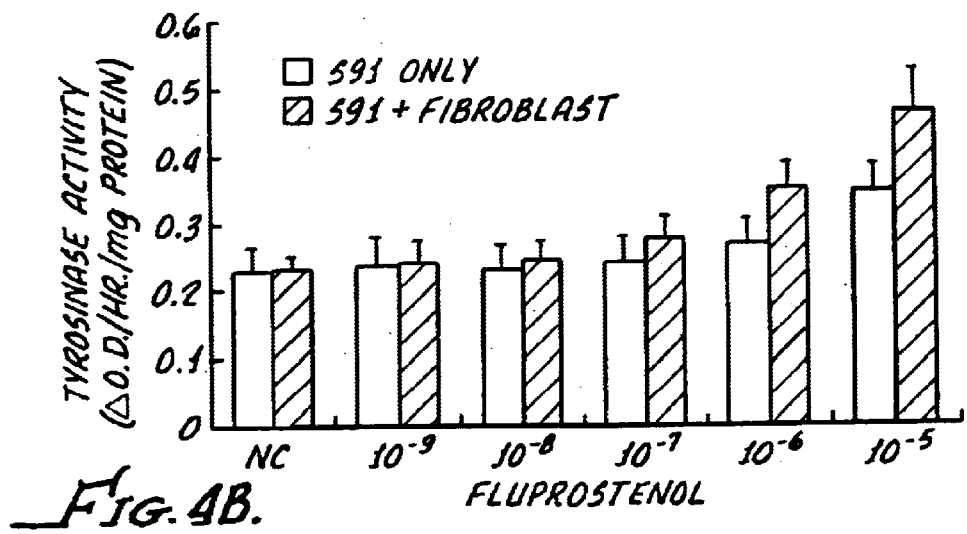
Figure 4C:
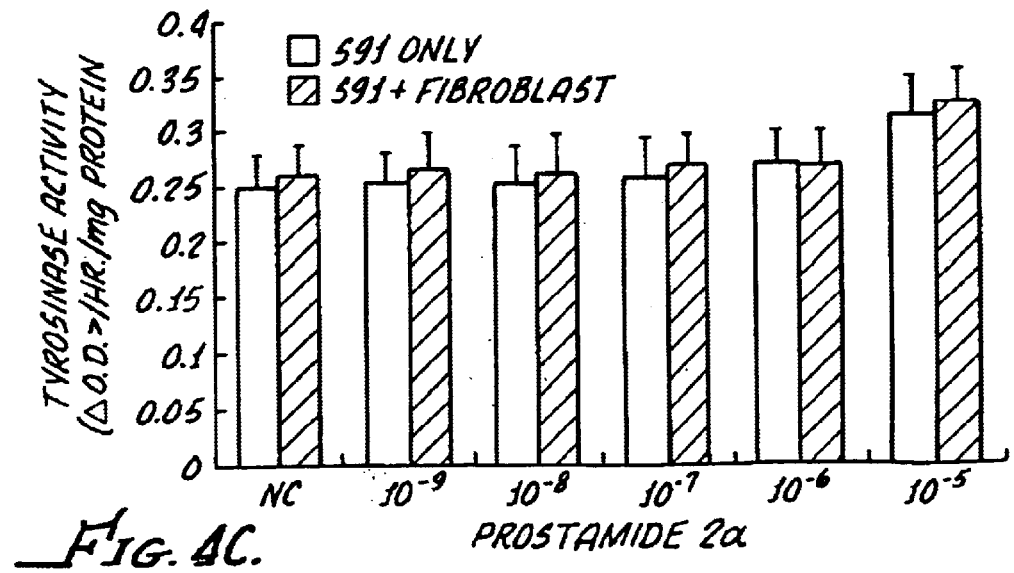

However, as shown in FIGS. 4A and 4B, respectively, when tyrosinase activity was used as a measure of melanin synthesis, a dose-dependent effect of latanoprost and fluprostenol was observed when fibroblasts were present. Prostamide, which lacks the carboxyl group and does not interact with the FP receptor, was unable to stimulate tyrosinase production either in the presence or absence of fibroblasts (FIG. 4C).

For latanoprost, it was found that both for DOPA oxidase activity and melanin formation in S91 cells not in transwell cultures at concentrations of up to $10^{-6}$ M, no appreciable change occurred. However, at $10^{-5}$ M, both an enhancement of tyrosinase activity and melanin formation were found. At this high concentration, specificity for the FP receptor is lost.

The invention has been exemplified in the foregoing examples; however the invention is defined solely by the claims which conclude this specification.

We claim:

1. A method to identify a compound having ocular hypotensive activity with reduced or absent ability to stimulate iridial hyperpigmentation comprising: contacting a test compound having ocular hypotensive activity and a population of melanin-producing cells co-cultured with fibroblasts or cells of a fibroblast-derived lineage displaying the prostaglandin FP receptor, and evaluating the ability of the compound to stimulate melanin formation; wherein a compound which fails to stimulate melanin formation to an equivalent or greater extent than an amount of latanoprost having the same hypotensive activity is identified as a compound having reduced or absent ability to stimulate iridial hyperpigmentation.

2. The method of claim 1 wherein said evaluating is performed by directly detecting the formation of melanin in said melanin-producing cells.

3. The method of claim 2 in which melanin formation is detected by measuring the absorbance of a solution containing a cell lysate of said melanin-producing cells after contact of said cells with a test compound at a wavelength characteristic of the presence of melanin.

4. The method of claim 2 in which melanin formation is detected by measuring the incorporation of at least one radioactive melanin precursor into melanin.

5. The method of claim 4 in which the melanin precursor is radiolabeled tyrosine.

6. The method of claim 2 in which melanin formation is detected by measuring the amount of tyrosinase activity contained within said melanin-producing cells after contact with said compound.

* * * * *